(12) United States Patent
Roberts et al.

(10) Patent No.: US 8,096,969 B2
(45) Date of Patent: Jan. 17, 2012

(54) PERITONEAL DIALYSIS METHODS AND APPARATUS

(75) Inventors: Martin Roberts, North Hills, CA (US); David B. N. Lee, Encino, CA (US)

(73) Assignees: The Regents of the University of California, Oakland, CA (US); The United States of America as represented by the United States Department of Veterans Affairs, Washington, DC (US)

( * ) Notice: Subject to any disclaimer, the term of this patent is extended or adjusted under 35 U.S.C. 154(b) by 0 days.

(21) Appl. No.: 12/773,227

(22) Filed: May 4, 2010

(65) Prior Publication Data

US 2010/0217181 A1      Aug. 26, 2010

Related U.S. Application Data

(62) Division of application No. 11/700,690, filed on Jan. 30, 2007.

(51) Int. Cl.
*A61M 1/00*     (2006.01)
(52) U.S. Cl. ............... 604/29; 604/27; 604/43
(58) Field of Classification Search ........... 604/27, 604/29, 43, 45, 518
See application file for complete search history.

(56) References Cited

U.S. PATENT DOCUMENTS

| | | | |
|---|---|---|---|
| 4,338,190 A | 7/1982 | Kraus et al. | |
| 4,581,141 A | 4/1986 | Ash | |
| 4,586,920 A | 5/1986 | Peabody | |
| 4,618,343 A | 10/1986 | Polaschegg | |
| 4,765,907 A | 8/1988 | Scott | |
| 4,790,319 A | 12/1988 | Slovak | |
| 5,846,533 A | 12/1998 | Prusiner et al. | |
| 5,944,684 A * | 8/1999 | Roberts et al. | 604/5.04 |
| 6,585,682 B1 | 7/2003 | Haraldsson et al. | |
| 2001/0012921 A1 | 8/2001 | Zicherman | |
| 2002/0112609 A1 | 8/2002 | Wong | |
| 2003/0113932 A1 * | 6/2003 | Sternberg et al. | 436/113 |
| 2004/0254513 A1 * | 12/2004 | Shang et al. | 604/5.01 |
| 2005/0085542 A1 | 4/2005 | Arduini | |
| 2005/0101901 A1 * | 5/2005 | Gura | 604/5.02 |
| 2005/0209563 A1 | 9/2005 | Hopping et al. | |
| 2005/0244909 A1 * | 11/2005 | Hamada et al. | 435/14 |
| 2005/0284815 A1 * | 12/2005 | Sparks et al. | 210/645 |

FOREIGN PATENT DOCUMENTS

WO      2005/025726      3/2005

* cited by examiner

*Primary Examiner* — Bhisma Mehta
(74) *Attorney, Agent, or Firm* — Fish & Associates, PC

(57) ABSTRACT

A peritoneal-based ("bloodless") artificial kidney processes peritoneal fluid without need for additional fluids ("waterless"). Fluid is separated into a protein-rich stream and a protein-free stream. The protein-rich stream is regenerated using a sorbent assembly, and its protein composition can be modified by removal of selected protein(s) ("dialysate-pheresis"). It is then reconstituted with additives and returned into the peritoneal cavity, thereby reducing protein-loss and providing oncotic-pressure for ultrafiltration. The protein-free stream is used to produce free water, and an alkaline or acid fluid for optimization of the composition of the regenerated stream. The unused protein-free stream can be used to "reverse flush" the separator to maintain its patency and the excess discarded for fluid-balance regulation. Compared to prior art, immobilization of urease allows more protein rich fluid to be regenerated and re-circulated into the peritoneal cavity for toxin removal and allows practicable development of portable and wearable artificial kidneys.

22 Claims, 3 Drawing Sheets

PERITONEAL DIALYSIS METHODS AND APPARATUS

This application is a divisional application of our copending U.S. patent application with the Ser. No. 11/700,690, which was filed 30 Jan. 2007, and claims priority to our U.S. provisional applications with the Ser. Nos. 60/763,254 and 60/763,337, both of which were filed 30 Jan. 2006.

FIELD OF THE INVENTION

The field of the invention is peritoneal dialysis.

BACKGROUND

Patients with inadequate kidney function require either dialysis or kidney transplantation for survival. When successful, kidney transplantation is the most ideal form of treatment since it restores continuous kidney function and returns patients to normal or near-normal life. However, the major problems in transplantation are the increasing shortage of donor kidneys relative to the expanding number of patient's with end-stage kidney failure, and the deterioration of the function of the transplant from causes including rejection, chronic (transplant) allograft nephropathy and the recurrence of the original kidney disease. There is also the life-long requirement for multiple medications with toxic side effects.

Most patients are placed on dialysis, with about 90% being treated by hemodialysis (HD) in the United States. This requires the circulation of a large amount of blood outside the patient's body, through a sealed compartment constructed of artificial membranes (the dialyzer, also known as the artificial kidney) and back into the patient. Fresh dialysate generated by a machine is pumped through the other side of the compartment extracting water-soluble metabolic wastes and excess fluid from the blood across the artificial membrane. The used dialysate exiting the dialyzer is discarded as waste. Patients are treated for three to four hours, two or three times a week, mostly in special treatment centers, staffed with nurses and technicians supervised by physicians. The channeling of large amount of blood out of the body (extracorporeal circulation) requires rigorous anticoagulation and monitoring. (The production of dialysate for each treatment requires about 90 gallons (340 liters) of water to prepare 30 gallons (120 liters) of dialysate) and a machine with an average weight of about 200 lb. (91 kg.). Because metabolic wastes and water are accumulated for 2-3 days between dialysis and are then rapidly removed within 3-4 hours, most patients feel sick after each treatment and may require hours to days to recover. Unfortunately, by then the next treatment is due.

About 10% of dialysis patients are treated with peritoneal dialysis (PD). In PD, fresh dialysate (usually 2 liters) is introduced into the abdominal (peritoneal) cavity of the patient, which is lined by the patient's peritoneal membrane. Water-soluble metabolic wastes and excess water in the blood circulating on the other side of the peritoneal membrane move into the dialysate by diffusion and convection. After a period of time, the spent dialysate is drained and discarded. Fresh dialysate is delivered into the peritoneal cavity to begin a new treatment cycle. Patients on continuous ambulatory peritoneal dialysis (CAPD) make 3-4 such exchanges every day during waking hours, and one additional nightly treatment cycle, which lasts 8-12 hours while, asleep. An increasing number of patients now undergo nocturnal dialysis using an automatic peritoneal cycler to carry out dialysis exchanges. Typically, 10 to 20 liters of dialysate are used for 5-10 exchanges (2-liters per exchange) through hours of sleep at night. The high cost of the dialysate almost always results in suboptimal dialysis, especially in patients in whom the residual kidney function is completely lost. Another drawback of the current PD is that significant amount of blood proteins leak across the peritoneal membrane into the dialysate and are discarded with the spent peritoneal dialysate (SPD).

Indeed, many of the problems and limitations of the prior art of peritoneal dialysis systems stem from the fact that the ability to regenerate the SPD is either non-existent or, if present, are subject to limitations. Such problems and limitations include, for example:

1) The dialysate usage is limited to about 10 to 20 liters of fresh dialysate per day, primarily due to the high cost of fresh dialysate. This, in turn, limits the amount of toxins that can be removed from the patient;
2) The proteins in the SPD are discarded with the SPD, resulting in a state of continuous protein-loss in patients already protein-malnourished from end-stage kidney failure;
3) Two or more connections are made to the dialysis system, in addition to the catheter;
4) The sodium concentration is fixed by the sodium level in the fresh commercial dialysate, and cannot be easily adjusted once treatment is started;
5) Commercial peritoneal dialysate contains lactate and has a pH of about 5.5, both of which can cause irritation and possible damage to the peritoneal membrane;
6) Commercial peritoneal dialysate contains glucose degradation products formed during sterilization by autoclaving. Additional degradation products are formed during storage of the dialysate prior to its use. These degradation products can also cause damage to the peritoneal membrane. Further, there are only three different glucose concentrations in the currently available dialysates, and the need for a change in glucose concentration requires a change to a new batch of dialysate containing a glucose concentration approximating that needed;
7) With present peritoneal dialysis equipment, beneficial agents, such as nutrients, hormones, antibiotics, and other therapeutic and health-enhancing agents cannot be readily infused;
8) The prior art systems that employ sorbent SPD regeneration contain a urease layer in which the urease can be displaced by protein in the SPD;
9) The prior art systems do not regulate and maintain sodium concentrations and pH in the dialysate at steady levels prescribed by physicians in individual patients.
10) The prior art systems that employ sorbent SPD regeneration to remove urea by using urease and a cation exchanger (such as zirconium phosphate), generate considerable amounts of carbon dioxide, but provide no means to remove this gas or other gases in a fluid-leak proof manner, while at the same time maintaining sterility in systems designed to function under different conditions, e.g., in a wearable system; and
11) The prior art sorbent SPD regeneration systems generate ammonium ions, which appear in the effluent of the sorbent assembly when the zirconium layer is exhausted. Such systems typically have no provision for continuously monitoring the effluent for ammonium ions, and they therefore cannot set off an audible, visual, vibratory or other form of alarm and/or turn off the system in response to this condition.

Regeneration and re-use of dialysis fluids has been contemplated. For example, U.S. Pat. No. 4,338,190 to Kraus et al (July 1982) teaches a re-circulating peritoneal dialysis system, as does U.S. Pat. No. 5,944,684 to Roberts and Lee (June 1999), and a 1999 article, Roberts, M., A Proposed Peritoneal-Based Wearable Artificial Kidney, *Home Hemodial Int*, Vol. 3, 65-67, 1999. (WO 2005/123230 to Rosenbaum et al.) teaches a re-circulating hemodialysis system. These and all other referenced extrinsic materials are incorporated herein by reference in their entirety. Where a definition or use of a term in an incorporated reference is inconsistent or contrary to the definition of that term provided herein, the definition of that term provided herein applies and the definition of that term in the reference does not apply.

Despite contemplating regeneration, reconstitution and re-use of dialysis fluids, the prior art does not describe especially practical ways of accomplishing that goal. The '190 patent, for example, does not use a sorbent cartridge, and therefore is much less effective than modern, sorbent based systems. The Roberts article and patent do contemplate use of a sorbent, but contemplated overly complicated devices that required separate processing and then recombining of protein containing and protein free (ultrafiltrate) streams. In addition, none of the prior art teaches a unit that could practically be worn by a user, and that included the numerous improvements described herein. For example, in the '684 patent:

1) A single peritoneal catheter is used for infusing and removal of dialysate from the patient's peritoneal cavity.
2) The dialysate flow rate through the peritoneal cavity is limited to 2 to 3 liters per hour, and the dwell volume in the peritoneal cavity is limited to a volume of about 250 to 1,000 ml.
3) The regenerating system is housed in a single assembly having multiple contiguous compartments containing urease and sorbents, such as zirconium phosphate, zirconium oxide and activated carbon/charcoal.
4) The urease in the regenerating system is not immobilized and can be displaced by proteins in the spent peritoneal dialysate (SPD), thus requiring that the SPD be separated into an ultrafiltrate and a protein fraction for purposes of regeneration and to thereafter be re-united prior to their recycling back into the patient's peritoneal cavity.
5) In the urease/zirconium ion exchange sorbent regeneration system, the sodium concentration increases, and the hydrogen concentration decreases in the regenerated dialysate with time as regeneration progresses, thereby developing progressively higher sodium and pH.
6) No provision is made for the evacuation of carbon dioxide produced during the regeneration process, particularly as the goal of the wearable kidney is to allow the patient unrestricted activity that will call for different bodily positions.
7) No provision is made for the use of dry glucose and in situ sterilization of glucose for immediate use in the regulation of ultrafiltration.
8) No provision is made for in-line monitors with "feedback loop" regulatory options of different components of the regenerated dialysate.
9) No provision is made for the regenerated peritoneal dialysate (RPD) to be enriched with nutrients, therapeutic agents, and other beneficial agents in dry or liquid form, sterilized in situ, and administered at programmed rates and timing patterns.
10) Removal of "noxious" or undesirable proteins, e.g., paraproteins, requires the separation of the protein fraction from the SPD.
11) No provision is made for removal of middle molecule uremic toxins.

Thus, there is still a need for improved systems that can function in multiple formats, including portable and wearable formats, in which peritoneal dialysate can be regenerated, reconstituted and re-used.

SUMMARY OF THE INVENTION

The present invention provides apparatus, systems and methods in which a peritoneal dialysate or other substantially non-blood containing fluid is withdrawn from the peritoneal cavity of a person or animal (generally referred to herein as a "person" or "patient" or "user"), the fluid is separated into a relatively protein-rich stream and a relatively protein-free stream. The relatively protein-rich stream is regenerated by processing to remove toxins, optionally reconstituted with additives, and then reintroduced into the peritoneal cavity. Use of a substantially immobilized urease allows a higher percentage of the fluid stream to be processed as the relatively protein-rich stream than in the prior art. For the first time it allows commercially practicable development of portable and even wearable dialysis units.

In one aspect of preferred embodiments the relatively protein-rich stream averages 95-98% (by vol) of the incoming stream from the peritoneal cavity of the user, which would mean that only about 2-5% (by vol) would comprise the relatively protein-free stream. In less preferred embodiments that percentage can be lower, preferably at least 90% (by vol), at least 40% (by vol), or even at least 15% (by vol). All practical types of protein fluid separators are contemplated, including especially hollow fiber filters, but the type of separator need not dictate that percentage. For example, a pump can be used to alter or otherwise control the percentage of relatively protein-rich stream to the incoming stream.

A suitable sorbent system regenerates the protein-rich stream by removing at least one toxin. The sorbent system preferably includes a urease or other enzyme(s) that is/are immobilized on a substrate with greater than Van der Waals forces. This immobilization of the urease prevents its displacement by proteins in the incoming protein-rich fluid stream. Previous systems, including our own, utilized urease which was not adequately immobilized, which meant that only a very small fraction (e.g. 2-3%) of the fluid could be processed as protein-rich fluid, and that most of the fluid reintroduced into the user was derived from the protein free portion.

Sorbents are preferably included in user-replaceable assemblies consisting of at least 100 gm of sorbents (dry weight). It is contemplated that an assembly could include one or more of zirconium phosphate, hydrated zirconium oxide, and activated carbon/charcoal. A sorbent assembly could additionally or alternatively target removal of one or more specific proteins from at least a portion of the relatively protein-rich stream (dialysis phoresis) and one or more middle molecule uremic toxins using additional sorbents.

In preferred embodiments at least some other processing occurs to the protein-rich stream. For example, a processing line can include a cation and/or anion exchanger, which alters concentration in at least a portion of the relatively protein-free stream of at least one of $H^+$, $OH^-$, $CO3^{--}$ and $HCO3^{--}$. Stabilization of the hydrogen ion concentration can also be enhanced by use of a zirconium phosphate layer as the final module in the sorbent cartridge.

The processing line can also advantageously include one or more of a sterilizer and a gas extractor. Gas extractors can be as simple as a vent (for portable systems), or more complicated, such as a hydrophilic/hydrophobic membrane filter (for wearable systems).

The relatively protein-free stream (ultrafiltrate) can be treated simply as waste, but in preferred embodiments has three other possible outcomes. Some of the protein-free stream can pass through an ion exchanger (anion, cation, or mixed bed), some of the stream can pass through a reverse osmosis filter, and/or some of the stream can be used to back flush the separator. In these latter three cases, the fluid is then added back to the relatively protein-rich stream.

Monitors and feedback loops are contemplated for maintaining a characteristic of the system, and for issuing a warning or shutting down the system when a measured characteristic falls outside of a desired range. Especially contemplated are monitoring and feedback for sodium concentration and pH. Monitoring and possible shutdown are especially contemplated for ammonia concentration.

Preferred embodiments also include at least one enrichment module that reconstitutes the protein-rich stream by adding at least one of glucose, potassium, calcium, and magnesium. In addition, it is contemplated that nutrients for long term alimentation and the administration of medications (e.g., antibiotics, chemotherapeutics), micronutrients, vitamins, hormones and any other therapeutic and health-maintaining and promoting agents and supplements could be added to the protein-rich stream as a way of introducing them into the patient (reverse dialysis). Delivery can be programmed on a continuous basis or on an on-demand basis, e.g., through a sensor-feedback-loop mechanism. An ultrasonic vibrator or other devices could be used to keep additives suspended, and/or facilitating their solvation. The fluid line that introduces the regenerated and reconstituted fluid back into the peritoneal cavity could use either the same or a different opening from that used to extract fluid, and could be operated concurrently or intermittently with the extraction fluid line.

For portable systems, the dry weight of the entire processing line (excluding a user-replaceable sorbent assembly) is preferably no more than 5 kg. The dry weight of user-replaceable sorbent assemblies is contemplated to be no more than 5 kg.

For wearable systems, the dry weight of the entire processing line (excluding a user-replaceable sorbent cartridge) is preferably no more than 1 kg. In such systems the dry weight of user-replaceable sorbent assemblies is contemplated to be no more than 1 kg. Wearable systems would generally also need a self-contained power supply. Such supplies should be sufficient to operate the processing line continuously for at least 8 hr, but could be designed for greater or lesser periods. To further enhance wearability, the internal and the external structure, functionality and material of the modules of the system can advantageously be designed to: 1) optimize aesthetic qualities and safety; 2) optimize dialysate regeneration and flow hydraulics; and 3) maximize the regenerative capacity and functional life of each module. To that end especially preferred modules are contemplated to be configured as non-rigid belts, packs or as apparel. The spent regenerative assembly or its individual components can be removed and replaced conveniently and safely (having in mind patients with impaired sensation and motor dexterity) using a sterility-maintaining undocking ("snap-out") and docking ("snap-in") mechanisms.

Preferred sorbent assemblies regenerate a relatively high percentage of fluid to the user over a relatively long period of time. Currently preferred embodiments, for example, will regenerate at least 80-90% of the substantially blood-free fluid as a protein-containing purified fluid over a period of 4 hours, and more preferably at least 80-90% over a period of 8 hours. Using another metric, currently preferred embodiments will re-circulate at least 20 liters of the substantially blood-free fluid as a purified fluid over a period of 10 hours, and more preferably at least 48 liters over a period of 24 hours. Using yet another metric, currently preferred embodiments will allow cumulative processing to occur at least 40 hours during a period of seven consecutive days, and more preferably 48, 56, 70, 126, or even almost 168 hours (full time except for replacement of power and chemical supplies).

In general, the inventive subject matter overcomes the various deficiencies in the prior art by providing a portable (and even wearable), automated peritoneal dialysis system based on the regeneration of a protein-containing dialysate. Because the system is peritoneal dialysis-based, it is "bloodless" and because the SPD is continuously regenerated, it is "waterless". Furthermore, by utilizing sorbent regeneration in a portable artificial kidney, the peritoneal proteins in the SPD can be returned to the patient.

Various objects, features, aspects and advantages of the present invention will become more apparent from the following detailed description of preferred embodiments of the invention, along with the accompanying drawings in which like numerals represent like components.

DETAILED DESCRIPTION

Figure 1:
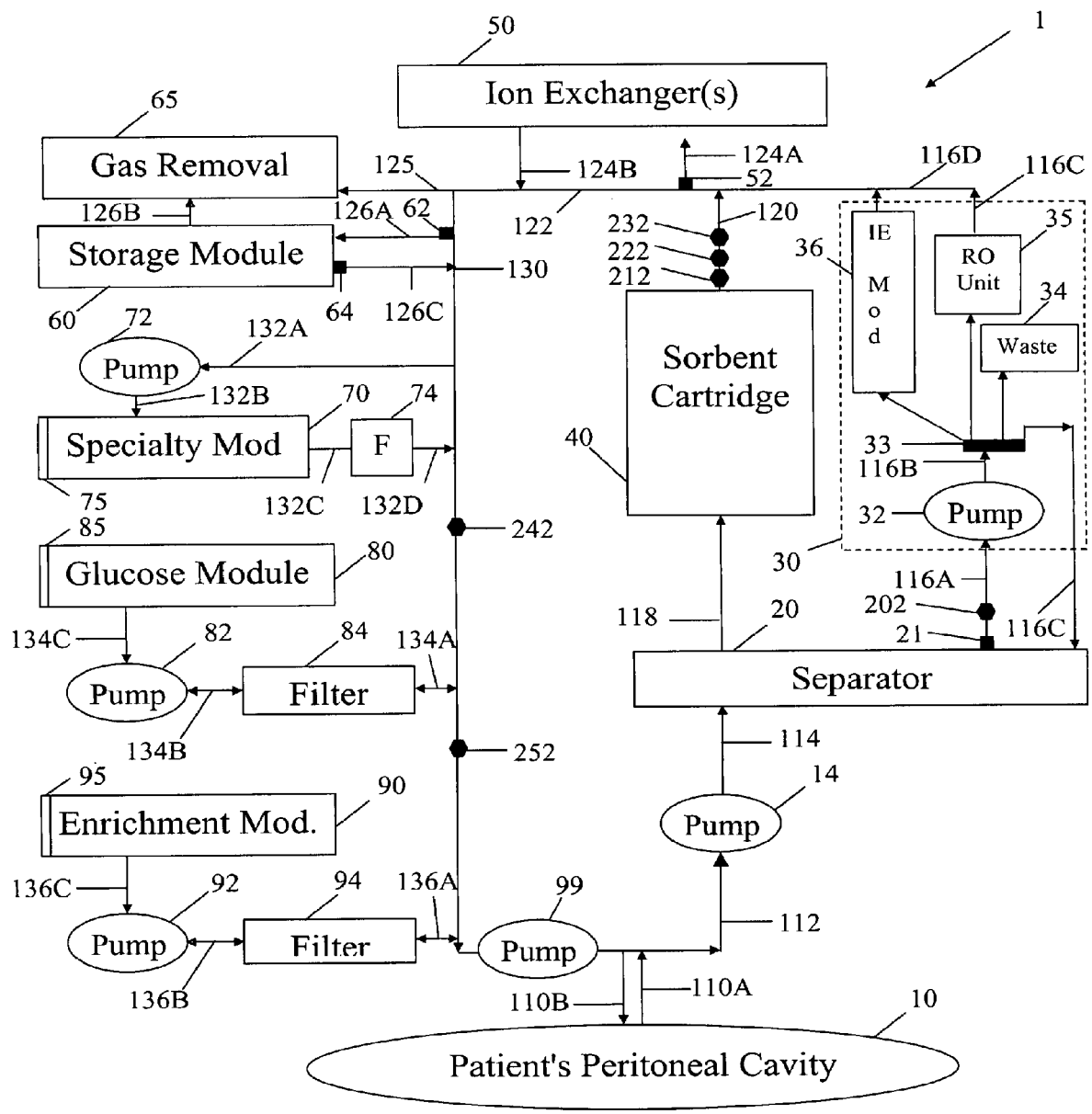
FIG. 1 is a schematic of a portable device coupled to a patient's peritoneal cavity, suitable for intermittent emptying and reintroduction of dialysate.

In FIG. 1 spent peritoneal fluid is withdrawn from a user/patient's peritoneal cavity 10 through catheter 110A, and processed along a processing line that includes a separator 20, an ultrafiltrate handling assembly 30, a sorbent assembly 40, and one or more ion exchangers 50, optional storage module 60, a specialty module 70, a glucose module 80, and an enrichment module 90. The fluid is then pumped back into the peritoneal cavity through in-flowing catheter 110B by pump 99. All of the components of FIG. 1, minus the catheters 110A, 110B and the peritoneal cavity 10 are sometimes referred to herein as artificial kidney 1. Thus, contemplated devices include a first fluid line that carries a fluid stream from a peritoneal cavity of a user, a processing line that includes a sorbent system to allow production of a modified dialysate stream, and a second line fluid that introduces at least some of the modified dialysate stream into the peritoneal cavity. It is also contemplated that the second fluid line is operable concurrently with the first fluid line.

Catheters 110A, 110B should be interpreted interactively as either two physically separate catheters, or a single catheter with one or more lumens. All of the catheters, the various pumps 14, 32, 72, 82, 92 and 99, and the various fluid conduits 112, 114, 116A, 116B, 116C, 116D, 118, 120, 122, 124A, 124B, 125, 126A, 126B, 126C, 130, 132A, 132B, 132C, 132D, 134A, 134B, 134C, 136A, 136B, and 136C can be entirely conventional. On the other hand, it is important that the components collectively support sufficient throughput of re-circulated fluid. For example, it is contemplated that the substantially blood-free fluid can be re-circulated as purified fluid at a rate sufficient to provide at least 18 liters of purified fluid over a 10 hour period, more preferably at least 20 liters, 30 liters, 40 liters and 48 liters over that same time period. In a 24 hour period it is contemplated that the substantially blood-free fluid can be re-circulated as purified fluid at a rate sufficient to provide at least 48 liters of purified fluid, more preferably at least 60 liters, still more preferably at least 72 liters, still more preferably at least 84 liters, and, still more preferably at least 96 liters.

To accomplish those ends it is contemplated that the various components will be sufficiently robust for processing to occur at least 40 hours during a period of seven consecutive days, which corresponds to 5 nights at 8 hours per night. More preferred embodiments provide for processing to occur at least 56 or 70 hours during a period of seven consecutive days. The 70-hour figure corresponding to 7 nights at 10 hours per night. Similarly, the various components of at least some embodiments should be sufficiently robust for processing to occur at least 126 hours during a period of seven consecutive days, which corresponds to 7 days at 22 hours per day.

Separator 20 comprises a hollow fiber or other material that can operate to split the incoming fluid into at least two streams, preferably a relatively protein-rich stream and a relatively protein-free stream. It is especially preferred that the relatively protein-rich stream ("protein-rich stream" for simplicity) has a significantly larger percentage of the fluid flow than was contemplated in the prior art. For example, instead of the protein-rich stream containing only 2-5% (by vol) of the input stream, and the protein-free stream (ultrafiltrate) containing 95-98% (by vol) (as in the prior art), separator 20 can advantageously maintain an average of at least 15% (by vol) of protein-rich stream relative to the input stream. In more preferred embodiments the separator 20 can maintain average protein-rich stream relative to input stream of at least 40% (by vol), at least 60% (by vol), at least 80% (by vol), at least 90% (by vol), at least 95% (by vol) and even at least 98% (by vol). , where the averages are taken over a meaningful processing period of an hour or more.

Over several hours, the split between the relatively protein-rich and relatively protein-free streams mentioned is a significant factor in determining how much of the substantially blood-free fluid is re-circulated as the purified fluid. Currently preferred embodiments re-circulate at least 80% over a period of 4 hours, more preferably at least 80% over a period of 4 hours, and still more preferably at least 80% over a period of 8 hours.

In contrast to the previous art, preferred embodiments can retain almost all of the autologous proteins in the protein-rich stream, thereby minimizing or eliminating protein-loss. Such proteins are, of course, non-sensitizing, and also have the benefit of providing oncotic pressure to retard trans-peritoneal (fluid) re-absorption, reducing or eliminating the need for the addition of glucose to the fluid being reintroduced into the peritoneal cavity 10.

The distribution of fluid between the relatively protein-rich and relatively protein-free streams can be controlled in various manners, including pumps and valves. In the embodiment of FIG. 1, pump 32 can be used to alter that distribution, at least to some extent. Valve 21 can also be used to that end. Therefore, contemplated devices include those having a pump that at least temporarily affects a ratio of the relatively protein-rich stream to the relatively protein-free stream.

The ultrafiltrate handling assembly 30 is contemplated to always include a provision for eliminating waste fluid from the system, but can additionally include apparatus for optional handling of the relatively protein-free fluid stream. FIG. 1 depicts an ultrafiltrate pump 32 that pumps fluid to valve 33, providing four outcomes:

1) Some and most likely most of the protein-free stream, will be pumped to the waste container 34. Most or all of the fluid in the waste container 34 will be disposed of, perhaps in a urinal or toilet;
2) Some of the protein-free stream can be pumped through a reverse osmosis unit 35, to provide a diluent that can be added back into the protein-rich stream;
3) Some of the protein-free stream can be pumped through a user-replaceable ion exchanger module 36 (anion, cation, or mixed bed) to alter pH and perhaps other factors. Output of the ion exchanger module 36 can also be added back into the protein-rich stream; and/or
4) Some of the stream can be used to back flush the separator, by using pump 32 to pump the fluid in waste container 34 back through the separator 20.

The sorbent assembly 40 is described in detail below with respect to FIG. 2.

Figure 3:
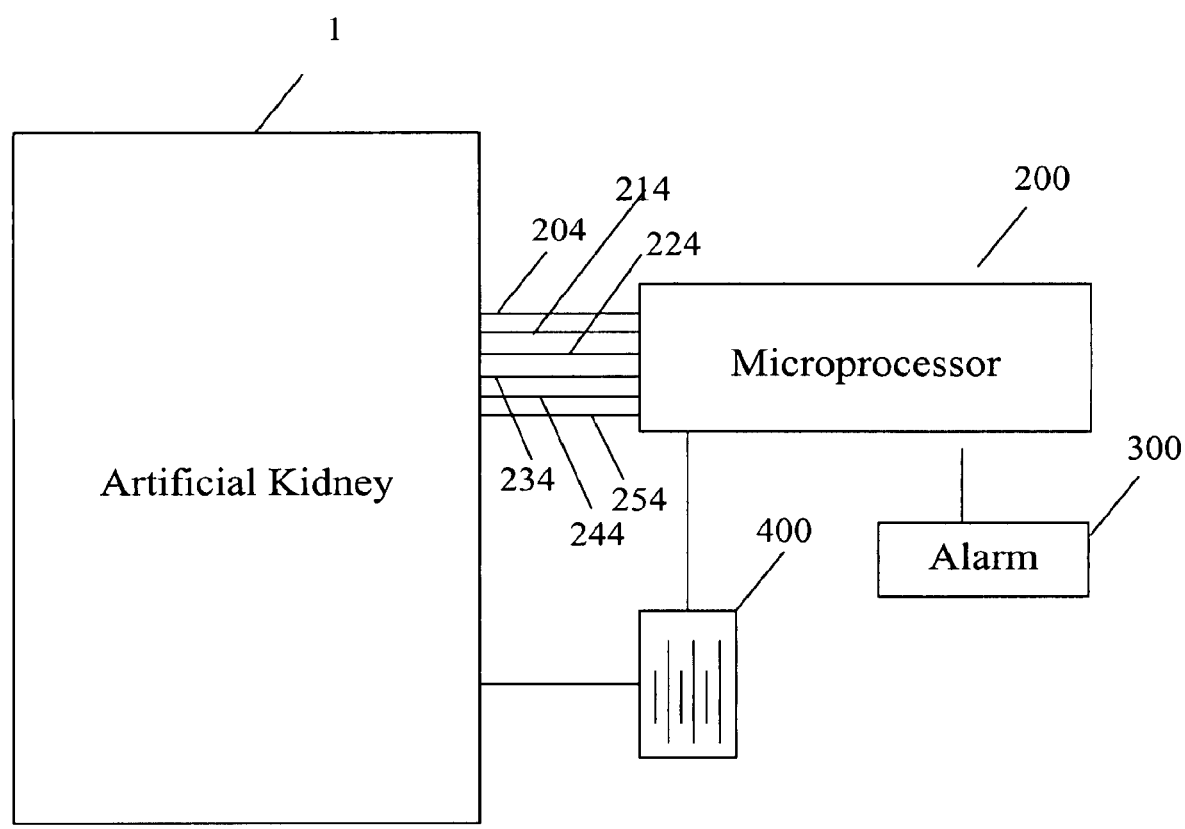
FIG. 3 is a schematic showing in-line monitoring and other controls for fluid flows within the device of FIG. 1.

Downstream of sorbent assembly 40 are one or more monitors (sensors) 202, 212, 222, 232, 242, and 252, all of which are more fully described with respect to FIG. 3.

Ion exchanger 50 is connected in parallel to fluid line 122 using shunt fluid lines 124A and 124B. Ion exchanger 50 can comprise an anion exchanger, a cation exchanger, or a mixed bed exchanger, and can advantageously alter a concentration of one, two, three or all four of $H^+$, $OH^-$, $CO_3^{--}$ and $HCO_3^{--}$ in the fluid passing through the exchanger, as well as other desired ions. One important use of ion exchanger 50 is to reduce sodium produced by conversion of urea within the sorbent assembly 40. Since the production of sodium will change over time, a control valve 52 controls how much of the flow from the sorbent assembly 40 enters the exchanger 50.

Storage module 60 is entirely optional. In either wearable or portable units, for example, fluid can be continuously withdrawn from the peritoneal cavity 10, processed, and then re-introduced into the cavity 10, all without any need for storage of the fluid being reintroduced. But where intermittent processing is desired, the storage module 60 advantageously retains the processed (or semi-processed) fluid until it is reintroduced. Contemplated storage capacities range from about 500 ml to about 3 liters. Unless the language context dictates otherwise, all ranges herein are to be interpreted as being inclusive of their endpoints.

Gas removal unit 65 is needed because the conversion of urea to ammonium carbonate the exchange of ammonium ions for hydrogen ions, and the reaction of the hydrogen ions with carbonate in the sorbent assembly 40, produce substantial amounts of carbon dioxide. Since $CO_2$ (and any other gases within the processing line) can be problematic, they should be removed from the system. In portable systems removal can be accomplished merely by venting, and the gas removal unit 65 should be interpreted as merely a vent. In wearable systems, however, venting is not practical because the user/patient might well be positioned from time to time that a vent would be upside down. In such cases gas removal can be accomplished using a hydrophobic or combination hydrophobic/hydrophilic filter, and the gas removal unit 65 should be interpreted as comprising such filter(s). Valves 62, 64 controls flow of fluid into and out of the storage module, respectively. An additional pump (not shown) can also be used.

Specialty module 70 is intended herein to provide additional processing not satisfied by the other modules. For example, specialty module 70 could provide the functionality of dialysis phoresis, removing one or more specific proteins from the fluid. Pump 72 can be used to control the amount of fluid passed through to specialty module 70, and filter 74 filters the fluid returning to the main processing flow.

Glucose module 80 adds glucose to the fluid being processed by means of a glucose supply conduit 134A, 134B, 134C. Two-way pump 82 facilitates this process, and indeed allows for variable control of glucose concentration in contrast to the current art, in which only three concentrations of glucose are available. Filter 84 eliminates unwanted particles and provides sterilization.

Enrichment module 90 can add substantially any desired enriching material, including for example one or more of glucose, potassium, calcium, and magnesium. Such materials can be added to the fluid being processed by means of an enrichment material supply conduit 136A using a two-way pump 92. It is contemplated that medications (e.g., antibiotics, chemotherapeutics), micronutrients, vitamins, hormones, and any other therapeutic and health maintaining and promoting agents and supplements, can also be introduced into the user/patient through the returning fluid. Introduction of such additional substances is known as reverse dialysis.

One or more of the glucose and enrichment materials can be supplied as a dry powder, and then dissolved in the fluid being processed. This is considered advantageous because dry glucose and other materials would tend to avoid degradation products that tend to be present in heat-sterilized fluids. In the embodiment of FIG. 1, dry glucose can be dissolved in the process fluid, and then filtered through a sterilizing filter 84. Similarly, dry enrichment chemicals can be dissolved in the process fluid, and then filtered through a sterilizing filter 94. Each of elements 70, 80 and 90 can optionally include a device, such as an ultrasonic vibrator (75, 85, and 95, respectively), that assists in dissolving and/or suspending the material being added.

In a typical example of intermittent processing, about two liters of suitable electrolyte solution would be introduced into a patient for a first treatment. After a set waiting period (e.g., 0-1 hour), the peritoneal outflow pump 14 is started to pump what is now the SPD along the first part of the processing line, and into the storage module 60 with a small fraction going into module 30. When the storage module 60 fills to approximately two liters, the storage module 60 is closed at valve 62. The storage module outflow valve is opened, the specialty module pump 72, the glucose pump 82, the enrichment pump 92, and the peritoneal inflow pump 99 are all started, and the now-processed fluid flows back into the user/patient until the storage module is empty. The process is then repeated. When convenient, the waste fluid in waste container 34 is emptied.

In a typical example of continuous processing, a system containing about 2 liters of a suitable electrolyte solution would be introduced into a patient for a first treatment. Instead of introducing that entire amount in to the patient all at once, a smaller bolus of fluid is optionally introduced to get the process started, (e.g. 500-1500 ml), and subsequently the fluid is slowly pumped into the patient, preferably at a rate of 34-67 ml/min. At the same time fluid is slowly withdrawn from the peritoneal cavity at approximately the same rate for processing as described herein.

Compared to current technology of using 10-20 liters of fresh dialysate for an 8-10 hour treatment, treatment using the device of FIG. 1 can provide 20-40 (or more) liters of regenerated dialysate over the same time period. This will bring about a two-fold or more increase in dialytic efficiency. Further, regeneration of the peritoneal proteins in the SPD would virtually eliminate protein-loss and, for the first time, remove protein-bound toxins without protein-loss. The recycling of the regenerated proteins also provides oncotic pressure and reduces or eliminates the amount of glucose required for fluid removal. Once initiated, the present invention requires no additional fresh dialysate, since dialysate would be regenerated from SPD as long as needed (theoretically, in perpetuity). In addition, the regenerated dialysate would have a physiological pH (7.4) and would contain the normal body base (bicarbonate). Both are considered advantages in maintaining normal body physiology and in preserving the peritoneal membrane. The currently available dialysate is acidic and contains lactate, both of which have been shown to be detrimental to the peritoneal membrane.

It is especially contemplated that the entire processing line, which comprises all of the components between catheters 110A and 110B, would advantageously be engineered for compactness and even wearability. Thus, for example, the entire processing line, excluding a user-replaceable sorbent cartridge, could be made to weigh no more than 8 kg, more preferably no more than 4 kg, and most preferably no more than 2 kg.

Figure 2:
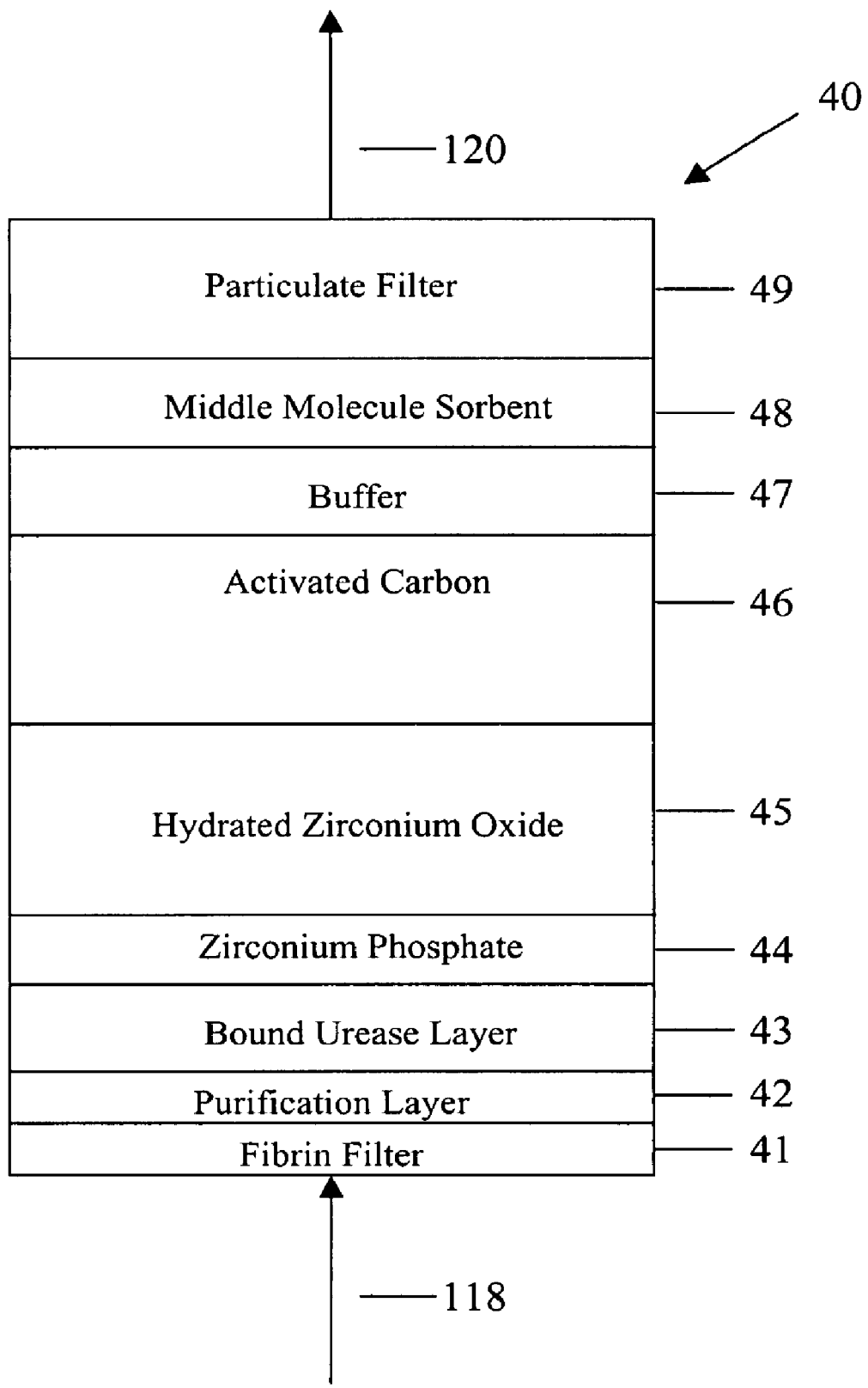
FIG. 2 is cross-sectional view showing the structure of the sorbent assembly of FIG. 1.

In FIG. 2 the sorbent assembly 40 includes in sequential flow order: a fibrin filter 41; a purification layer 42; a bound urease layer 43; a zirconium phosphate layer 44 a hydrated zirconium oxide layer 45; an activated carbon layer 46; a buffer layer 47 to stabilize pH; a middle molecule sorbent layer 48, and finally a particulate filter 49. Those skilled in the art will appreciate that one or more of the layers can optionally be eliminated, and indeed the various materials shown as residing in layers of a single assembly could be housed in separate modules or cartridges, and/or included in different sequences from that expressly shown herein.

Preferred fibrin filters will be capable of filtering out other particulates (e.g. mucus, semisolids and solids)

Of particular interest is that the urease in the sorbent assembly is immobilized onto a matrix in a fashion that allows easy sterilization without significant loss of its activity and renders the enzyme resistant to displacement by proteins in the fluid being processed. Immobilization is defined here to mean that the urease is attached to a substrate with a force greater than Van der Waals forces, and can occur in any number of ways, including possibly covalent and/or ionic bonding of the urease to a substrate.

The middle molecule sorbent layer 48 can comprise any suitable material or combination of materials. The concept of middle molecules uremic toxins and materials for removing middle molecules are discussed in: Winchester, James F., et al., The Potential Application of Sorbents in Peritoneal Dialysis, *Contributions to Nephrology,* Vol. 150, 336-43, 2006; Vanholder, R., et al., Review On Uremic Toxins, Classification, Concentration, And Interindividual Variability, *Kidney International,* Vol. 63,1934-1943, 2003; and Chiu A, et al., Molecular adsorbent recirculating system treatment for patients with liver failure: the Hong Kong experience, *Liver International,* Vol. 26, 695-702, 2006.

Sorbent assemblies 40 can be provided in many different sizes. In most instances it is contemplated that individual assemblies will contain at least 100 gm of sorbent, with larger sizes depending upon intended use, all weights herein being given in dry weight. For example, sorbent assemblies for portable units might weigh no more than 2.0 kg, and more preferably no more than 1.5 kg. This compares favorably with typical hemodialysis sorbent assemblies that weigh about 2.5 kg. For wearable units, the sorbent assemblies would likely weigh no more than 2 kg, more preferably no more than 1 kg, and most preferably no more than 0.5 kg.

Sorbent assemblies 40 can also be provided in many different shapes. For portable units the shape is not particularly important, but for wearable units it is contemplated that the assemblies would be relatively flat, and possibly even slightly concave on one side, to facilitate carrying of the assemblies in a belt.

In FIG. 3, the artificial kidney 1 operation of the valves and the activation/deactivation of pumps, as well as the overall control of the system and methods of the present invention, are advantageously controlled by a microcomputer 200, so that the various operations/treatments occur automatically. Among other things such control involves monitors and feedback loops that maintain concentrations of select components within desired ranges, and possibly shut down the unit when certain specific conditions are detected.

To that end microprocessor 200 can receive signals from a sodium monitors 202 and 212, and through a feedback loops 204 and 214, control ion exchanger valves 33 and 52, respectively to maintain an average sodium concentration of at least a portion of the relatively protein-rich stream within a desired range over a period of at least 1 hour. Preferred concentrations of sodium in any fluid re-introduced into the user/patient is 135-145 meq/l, and most preferably 140 meq/l.

Similarly, microprocessor 200 can receive signals from a pH monitor 222, and through a feedback loop 224 control pump 32 to maintain a pH within a desired range over a period of at least 1 hour. Currently preferred pH is between 6.5 and 8, and most preferably about 7.4.

Microprocessor 200 also preferably receives signals from ammonia detector 232 and feedback loop 234 that triggers an action when an ammonia concentration in at least a portion of the relatively protein-rich stream is greater than a desired upper limit, such as 2 mg %. The most likely action is shutting down of the system by directing pump 14 and 99 to stop operating, and/or sounding an alarm 300 because presence of ammonia means that the sorbent assembly is spent and must be replaced. Shutting down of the system could be accomplished in any suitable way.

Microprocessor 200 can also receive signals from a glucose detector 242, and through a feedback loop 244 control pump 82 to maintain average glucose concentration within a desired range over a period of at least 1 hour. Currently preferred glucose concentrations are between 1.5 and 4.25 g/dl, and most preferably about 2 g/dl. It is also contemplated that the user/patient could control glucose concentrations manually to at least some extent.

Still further, microprocessor 200 can receive signals from potassium, calcium, or magnesium detectors, collectively 252, and through a feedback loop 254 control pump 92 to maintain average concentrations of one or more of these elements within a desired range over a period of at least 1 hour. Currently preferred potassium concentrations are between 0 and 4 meq/L, and most preferably about 1 meq/L. Currently preferred calcium concentrations are between 2.5 and 4 meq/L, and most preferably about 3.5 meq/L. Currently preferred magnesium concentrations are between 1 and 3 meq/L, and most preferably about 2.5 meq/L.

Power source 400 is the power source that powers artificial kidney and related electronics. This is mostly likely line current for a portable unit, and a user replaceable rechargeable battery pack for a wearable unit. In any event, FIG. 3 the power source is shown as a battery because even portable units can advantageously include a battery pack that acts as an uninterruptible power supply. Power source 400 should preferably have sufficient power to operate the processing line continuously for at least 5 hours, more preferably at least 8 hours, and still more preferably at least 12 hours. In some cases it may be desirable to have battery life of at least 15, and in other cases at least 24 hours. The rationale for those time periods is that user/patients with wearable units will likely change their sorbent assemblies about ever four hours during the day, and up to 10 hours when they are sleeping at night. In other cases user/patients may be on a trip or have some other circumstance where longer battery life may be desirable.

Embodiments of the inventive subject matter have numerous benefits over the prior art, including for example:

1) Manufacture of the regenerative assembly from interconnected modules (whether housed in one single unit or several different units) allows designers to: (a) optimize portability, aesthetic qualities and safety; (b) optimize dialysate regeneration and flow hydraulics; and (c) maximize the regenerative capacity and functional life of each module.
2) Recycling of 2-4 liters of fluid per hour can provide much better removal of toxins than the 10-20 liters now used for each treatment in the current intermittent methods;
3) Recycling of dialysate is much less expensive than purchasing and consuming an equal volume of fresh dialysate;
4) Once treatment is initiated, there is no requirement for additional dialysate supply; it is therefore "waterless" as that term is used in some of the literature;
5) Proteins in the SPD are conserved instead of being discarded, thereby enhancing the removal of protein-bound toxins and providing oncotic pressure, all without triggering immune events;
6) The number of connections can be greatly reduced, such as by eliminating connections to a fresh dialysate supply source as required with currently available peritoneal dialysate cyclers;
7) Through incorporation of modules customized for specific protein removal, contemplated embodiments can provide plasmaphoresis of noxious and undesirable proteins;
8) Concentrations of sodium, glucose, nutrients, hormones, antibiotics, and other substances can all be controlled during treatment, using in-line monitors, all without degradation byproducts;
9) The regenerated peritoneal dialysate, in addition to its protein content, has the unique features of exhibiting a normal pH and contains bicarbonate rather than lactate or other metabolizable anions. The composition of bicarbonate, sodium, pH and other cations and anions can be altered, singly or in combination, according to specific prescriptions for the management of disorders including electrolytes, minerals and acid-base abnormalities.
10) The automated portable artificial kidney of the present invention makes possible a reduction in demand for specialized physical facilities, for medical personnel and for obligatory patient labor (thereby, avoiding patient treatment fatigue). No permanent treatment space is required, and medical and technical consultation can be scheduled on a regular basis, e.g., monthly.
11) Patient involvement consists mainly to setting up the portable artificial kidney nightly or with the wearable changing cartridges and the glucose and enrichment modules every 4 hours.

Thus, specific embodiments and applications of peritoneal dialysis apparatus, systems and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A peritoneal dialysis system, comprising:
    a first fluid line that carries a fluid stream from a peritoneal cavity of a user;
    a separator that separates the fluid stream into a relatively protein-rich stream and a relatively protein-free stream, wherein the relatively protein-rich stream averages at least 15% (by vol) of the fluid stream over at least some period of time; and
    a processing line that includes a sorbent system that is configured to remove at least one toxin from at least some of the protein-rich stream to thereby allow production of a modified dialysate stream;
    a second fluid line that introduces at least some of the modified dialysate stream into the peritoneal cavity; and
    wherein at least some of the sorbent system includes an enzyme that is immobilized on a substrate with greater than Van der Waals forces.

2. The peritoneal dialysis system of claim 1, wherein the relatively protein-rich stream averages at least 40% (by vol) of the fluid stream from the peritoneal cavity over the at least some period of time.

3. The peritoneal dialysis system of claim 1, wherein the relatively protein-rich stream averages at least 90% (by vol) of the fluid stream from the peritoneal cavity over the at least some period of time.

4. The peritoneal dialysis system of claim 1, wherein the separator comprises a hollow fiber filter.

5. The peritoneal dialysis system of claim 1, further comprising a pump that at least temporarily affects a ratio of the relatively protein-rich stream to the relatively protein-free stream.

6. The peritoneal dialysis system of claim 1, wherein the sorbent system comprises a user-replaceable assembly having at least 100 gm of a sorbent.

7. The peritoneal dialysis system of claim 6, wherein the user-replaceable sorbent assembly has a dry weight of no more than 5 kg.

8. The peritoneal dialysis system of claim 6, wherein the user-replaceable sorbent assembly has a dry weight of no more than 2 kg.

9. The peritoneal dialysis system of claim 1, wherein the processing line includes a processor comprising at least one of a cation exchanger and an anion exchanger, which alters a concentration in at least a portion of the relatively protein-free stream of at least one of $H^+$, $OH^-$, $CO_3^{--}$ and $HCO_3^{--}$.

10. The peritoneal dialysis system of claim 1, wherein the processing line includes a gas extractor disposed to operate upon at least a portion of the relatively protein-rich stream.

11. The peritoneal dialysis system of claim 1, further comprising a monitor that measures a characteristic of the system.

12. The peritoneal dialysis system of claim 1, further comprising a sodium monitor and feedback loop that maintains an average sodium concentration of at least a portion of the relatively protein-rich stream within a desired range over a period of at least 1 hour.

13. The peritoneal dialysis system of claim 1, further comprising a pH monitor and feedback loop that maintains an average pH of at least a portion of the relatively protein-rich stream within a desired range over a period of at least 1 hour.

14. The peritoneal dialysis system of claim 1, further comprising an ammonia detector and feedback loop that triggers an action when an ammonia concentration in at least a portion of the relatively protein-rich stream is greater than a predetermined value.

15. The peritoneal dialysis system of claim 1, further comprising a glucose addition module, and at least one enrichment module that collectively adds at least two of potassium, calcium, and magnesium to at least a portion of the relatively protein-rich stream.

16. The peritoneal dialysis system of claim 1, further comprising a unit that targets removal of a specific protein from at least a portion of the relatively protein-rich stream.

17. The peritoneal dialysis system of claim 1, further comprising an ultrasonic vibrator that operates upon at least a portion of the relatively protein-rich stream and that is configured to facilitate solvation of additives.

18. The peritoneal dialysis system of claim 1, wherein the second fluid line is operable concurrently with the first fluid line.

19. The peritoneal dialysis system of claim 1, wherein the processing line, excluding a user-replaceable sorbent cartridge, has a dry weight of no more than 5 kg.

20. The peritoneal dialysis system of claim 1, wherein the processing line excluding a user-replaceable sorbent assembly has a dry weight of no more than 2 kg.

21. The peritoneal dialysis system of claim 1, wherein the processing line includes a gas removal unit disposed to operate upon at least a portion of the relatively protein-rich stream.

22. The peritoneal dialysis system of claim 1, further comprising a power source sufficient to operate the processing line continuously for at least 7 hours.

* * * * *